United States Patent [19]
Wellinga et al.

[11] Patent Number: 4,920,135
[45] Date of Patent: * Apr. 24, 1990

[54] INSECTICIDAL UREAS AND THIOUREAS

[75] Inventors: Kobus Wellinga; Rudolf Wulder, both of Weesp, Netherlands

[73] Assignee: Duphar International Research B.V., Weesp, Netherlands

[*] Notice: The portion of the term of this patent subsequent to Feb. 24, 1993 has been disclaimed.

[21] Appl. No.: 306,928

[22] Filed: Feb. 7, 1989

Related U.S. Application Data

[60] Division of Ser. No. 867,695, May 28, 1986, Pat. No. 4,833,151, which is a continuation of Ser. No. 665,508, Oct. 30, 1984, Pat. No. 4,607,044, which is a continuation of Ser. No. 302,591, Sep. 15, 1981, abandoned, which is a continuation of Ser. No. 35,978, May 4, 1979, abandoned, which is a division of Ser. No. 717,633, Aug. 26, 1976, Pat. No. 4,166,124, which is a division of Ser. No. 522,058, Nov. 8, 1974, Pat. No. 3,989,842, which is a division of Ser. No. 354,393, Apr. 25, 1973, Pat. No. 3,933,908, which is a division of Ser. No. 143,668, May 14, 1971, Pat. No. 3,748,356.

[30] Foreign Application Priority Data

May 15, 1970 [NL] Netherlands .......................... 7007040

[51] Int. Cl.$^5$ ...................... A01N 43/30; A01N 47/28

[52] U.S. Cl. .................................... 514/344; 514/353; 514/584; 514/585; 514/587; 514/588; 514/594; 514/595

[58] Field of Search ............... 514/344, 353, 584, 585, 514/587, 588, 594, 595

[56] References Cited

U.S. PATENT DOCUMENTS 3,793,213  2/1974  Taber et al. .......................... 252/107
4,607,044  8/1986  Wellinga et al. ..................... 514/383
4,833,151  5/1989  Wellinga et al. ..................... 514/344

Primary Examiner—Leonard Schenkman
Attorney, Agent, or Firm—Finnegan, Henderson, Farabow, Garrett & Dunner

[57] ABSTRACT

Certain organic compounds derived from urea or thiourea having insecticidal activity and methods of their preparation are disclosed. The compounds according to the invention have been found to interfere with the mechanism of metamorphoses which occurs in insects. Hence, the substances according to the invention are specifically active against insects. Owing to this specificity and because of the absence of phytotoxicity effects, the compounds of this invention are of prime importance.

3 Claims, No Drawings

INSECTICIDAL UREAS AND THIOUREAS

This is a division of application Ser. No. 06/867,695, filed May 28, 1986, now Pat. No. 4,833,151, which is a continuation of Ser. No. 655,508, filed Oct. 30, 1984, now Pat. No. 4,607,044, which is a continuation of Ser. No. 302,591, filed Sept. 15, 1981, now abandoned, which is a continuation of Ser. No. 35,978, filed May 4, 1979, now abandoned, which is a division of Ser. No. 717,633, filed Aug. 26, 1976, now Pat. No. 4,166,124, which is a division of Ser. No. 522,058, filed Nov. 8, 1974, now Pat. No. 3,989,842, which is a division of Ser. No. 354,393, filed Apr. 25, 1973, now Pat. No. 3,933,908, which is a division of Ser. No. 143,668, filed May 14, 1971, now Pat. No. 3,748,356.

U.S. Pat. No. 3,450,747 describes that the compound N-(3,4-dichlorobenzoyl)-N'-(3,4-dichlorophenyl) urea has a herbicidal and/or insecticidal activity.

It has now been found that a group of new compounds indicated hereinafter have a strong insecticidal activity.

The above-mentioned known substance proves not to have such activity.

We are concerned here with new compounds of the formula

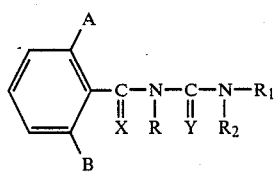

where

A is a hydrogen atom, a halogen atom, a methyl group or a methoxy group,

B also represents a hydrogen atom, a halogen atom, a methyl group or a methoxy group, with the proviso that A and B do not both represent a hydrogen atom, X and Y each represent an oxygen atom or a sulfur atom, R is a hydrogen atom, an alkyl group, a hydroxy group, an alkoxy group, an alkoxymethyl group, an acyl group or an alkoxycarbonyl group, $R_1$ is a hydrogen atom, an alkyl group which may be substituted with halogen, with alkoxy, with alkylthio or with cyano, a 1-cyanoalkenyl group, a benzyl group which may be substituted with halogen, a hydroxy group, an alkoxy group, an acyl group, an alkoxycarbonyl group, an alkoxythiocarbonyl group, an alkylsulfonyl group or a phenylsulfonyl group, whilst furthermore R and $R_1$ together with the group

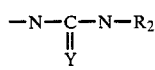

indicated in the above formula may form a ring system, and $R_2$ represents a substituted or non-substituted phenyl group or a pyridyl group which may be substituted with halogen, with nitrocyano or with halogenated alkyl. The aforementioned ring system may be represented by any of the following formulae

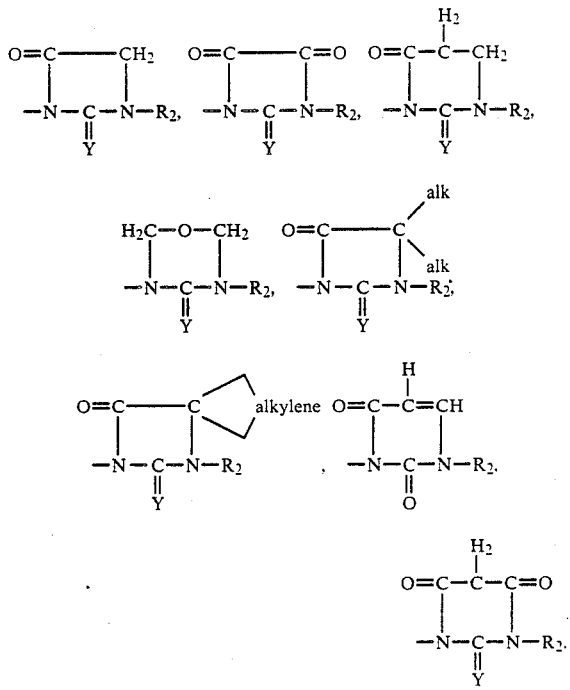

In these formulae Y and $R_2$ have the aforementioned meanings, alk is an alkyl group and alkylene is a bivalent saturated alkylene group.

If $R_2$ is a substituted phenyl group, the phenyl group contains at least one substituent chosen from the group consisting of:

(a) 1-3 halogen atoms, (b) 1-2 alkyl group, possibly substituted with halogen, hydroxy, alkoxy, alkylthio, dialkyl amino, alkylsulphonyl and phenyl, (c) tri- or tetramethylene, (d) a cycloalkyl group, possibly substituted with halogen or cyano, (e) 1-2 nitro groups or cyano groups or alkoxy groups, (f) a dioxymethylene or dioxyethylene group, (g) an acyl group, which may be substituted with halogen, (h) an alkyl sulfonyl, phenyl sulfonyl, alkylthio, phenylthio or phenoxy group, which groups may be substituted with halogen, (i) a sulfonamide group, which may alkylated, and (k) a phenyl group, which may be substituted with halogen, nitro, cyano and halogenated alkyl.

The insecticidal activity of the above group of substances have been found in a biological evaluation investigation in which test solutions and test suspensions of the active substances have been examined for biocidal activity with respect to inter alia *Aedes aegypti, Leptinotarsa decemlineata, Pieris brassica, Musca domestica* and *Schistocerca gregaria*. Each active compound has been tested in various concentrations, starting from a maximum concentration of 100 mg of active substance per liter of test liquid and then, according to the activity found, reducing the concentration successively to 30, 10, 3, 1, 0.3 and 0.1 mg of active substance per liter of test liquid.

The results of the evaluation investigation show that the aforementioned compounds according to the invention are active against insects in the larval stage, and that the active substance is to be absorbed by the larva via its stomach.

The compounds according to the invention are active against, amongst other pests, caterpillars and larvae of flies, beetles, mosquitoes, locusts, cockroaches and bugs.

More particularly it has been found that the substances according to the invention have a completely new and hiterto unknown mechanism of activity, for it has been found that the substances according to the invention interfere with the mechanism of metamorphoses which occur in insects. Hence the substances according to the invention are specifically active against insects. Owing to this specificity and because of the absence of phytotoxicity effects the compounds according to the invention are of prism importance.

From the biological evaluation investigation on which the invention is based it has been found that especially the compounds of the following formula have a strong insecticidal activity:

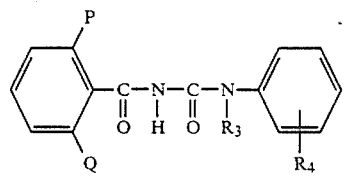

where

P and Q may be equal or different and each represent a chlorine atom, a fluorine atom or a methyl group, $R_3$ represents a hydrogen atom, an alkyl group, a benzyl group, an acyl group or an alkoxycarbonyl group, $R_4$ represents from 0-3 substitutes selected from the group comprising from 1 to 3 halogen atoms, an alkyl group which contains from 1 to 15 carbon atoms and may be substituted with one or more halogen atoms or with a phenyl group, a cycloalkyl group which may be substituted with at least one halogen atom a nitro group, a cyano group, a phenyl group, a thiophenyl group, a benzoyl group, a thioalkyl group and an alkylsulfonyl group.

This applies in particular to the substances of the above formula in which $R_3$ represents a hydrogen atom or a lower alkyl group.

A highly potent insecticidal activity has been found in compounds according to the invention which satisfy the formulae

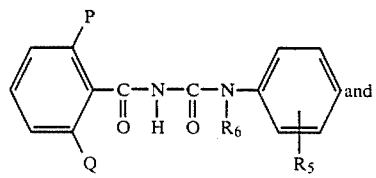

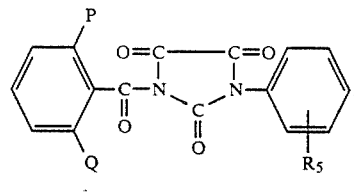

where

P and Q may be equal or different and each represent a chlorine atom, a fluorine atom or a methyl group, $R_6$ is a hydrogen atom or a lower alkyl group and $R_5$ represents 1–3 substituents selected from the group comprising 1–3 halogen atoms, an alkyl group which contains from 1 to 15 carbon atoms and may be substituted with at least one halogen atom, and a cycloalkyl group which may be substituted with at least one halogen atom. More particularly it has been ascertained that the highest activity is found in the compounds of the above formulae in which $R_5$ represents one or two substituents in the position 3 or the position 4 or the positions 3 and 4 of the phenyl group.

It has further been found that a strong insecticidal activity is also present in the substances according to the invention which may be represented by the formula

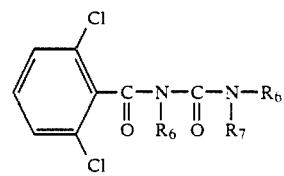

where $R_6$ is a hydrogen atom or a lower alkyl group and $R_7$ represents a phenyl group which may be substituted.

Representatives of this group of substances possessing the highest activity may be indicated by the formula

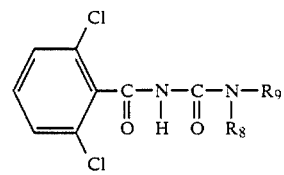

where $R_9$ is a hydrogen atom or a methyl group and $R_8$ represents a phenyl group which may be substituted with 1-3 halogen atoms, with an alkyl group, with a cyclo-alkyl group, with a nitro group, with a tetramethylene group, with a methylenedioxy group or with a methylsulfonyl group.

Examples of compounds having the highest activity are:
N-(2,6-dichlorobenzoyl)-N'-(3,4-dichlorophenyl)urea, melting point 238° C.,
N-(2,6-difluorobenzoyl)-N'-(3,4-dichlorophenyl)urea, melting point 253° C.,
N-(2,6-dimethylbenzoyl)-N'-(3,4-dichlorophenyl)urea, melting point 197° C.,
N-(2,6-dichlorobenzoyl)-N'-(4-chlorophenyl)urea, melting point 236° C.,
N-(2,6-dimethylbenzoyl)-N'-(4-chlorophenyl)urea, melting point 190°–191.5° C.,
N-(2,6-dichlorobenzoyl)-N'-(2,4-dichlorophenyl)urea, melting point 238° C.,
N-(2,6-dichlorobenzoyl)-N'-(4-cyclopropylphenyl)urea, melting point 208° C.,
N-(2,6-dichlorobenzoyl)-N'-(3-chloro-4-iodophenyl)urea, melting point 254° C.,
N-(2,6-dichlorobenzoyl)-N'-(3-chloro-4-bromophenyl)urea, melting point 240° C., N-(2,6-dichlorobenzoyl)-N'-(4-isopropylphenyl)urea, melting point 204° C., N-(2,6-dichlorobenzoyl)-N'-(3,4-dibromophenyl)urea, melting point 252° C., N-(2,6-dichlorobenzoyl)-N'-(4-fluorophenyl)urea, melting point 212° C.

N-(2,6-dichlorobenzoyl)-N'-(3-trifluoromethylphenyl)urea, melting point 230° C., N-(2,6-dichlorobenzoyl)-N'-(4-n.butylphenyl)urea, melting point 190° C., N-(2,6-dichlorobenzoyl)-N'-(3-chloro-4-methylsulfonylphenyl)urea, melting point 245° C., N-(2,6-dichlorobenzoyl)-N'-(4-t.butylphenyl)urea, melting point 212° C.

N-(2,6-dichlorobenzoyl)-N'-(3,4-difluorophenyl)urea, melting point 216° C.

N-(2,6-dichlorobenzoyl)-N'-(2,4-difluorophenyl)urea, melting point 248° C.

N-(2,6-dichlorobenzoyl)-N'-(4-bromophenyl)urea, melting point 236° C.

N-(2,6-dichlorobenzoyl)-N'-(2,5-difluoro-4-bromophenyl)urea, melting point 270° C.

N-(2,6-dichlorobenzoyl)-N'-(4-iodophenyl)urea, melting point 215° C.

N-(2,6-dichlorobenzoyl)-N'-(3-fluoro-4-chlorophenyl)urea, melting point 225° C.

N-(2,6-dichlorobenzoyl)-N'-(4-phenylphenyl)urea, melting point 260° C.

N-(2,6-dichlorobenzoyl)-N'-(4-cyanophenyl)urea, melting point 248° C.

N-(2,6-dichlorobenzoyl)-N'-(3-fluoro-4-bromophenyl)urea, melting point 228° C.

N-(2,6-dichlorobenzoyl)-N'-(3-fluoro-4-iodophenyl)urea, melting point 220° C.

N-(2,6-dichlorobenzoyl)-N'-(2-fluoro-4-iodophenyl)urea, melting point 256° C.

N-(2,6-dichlorobenzoyl)-N'-(4-n.propylphenyl)urea, melting point 194° C.

N-(2,6-dichlorobenzoyl)-N'-(4-trifluoromethylphenyl)urea, melting point 214° C.

N-(2,6-dichlorobenzoyl)-N'-(3-cyclopropylphenyl)urea, melting point 208° C.

N-(2,6-dichlorobenzoyl)-N'-(2-methyl-4-chlorophenyl)urea, melting point 206° C.

N-(2,6-dichlorobenzoyl)-N'-(4-sec.butylphenyl)urea, melting point 168° C.

N-(2,6-dichlorobenzoyl)-N'-(4-iso-butylphenyl)urea, melting point 215° C.

N-(2,6-dichlorobenzoyl)-N'-(4-ethylphenyl)urea, melting point 228° C.

N-(2,6-dichlorobenzoyl)-N'-(4-n.dodecylphenyl)urea, melting point 117° C.

N-(2,6-dichlorobenzoyl)-N'-4-benzylphenyl)urea, melting point 207° C.

N-(2,6-dichlorobenzoyl)-N'-(3,4-dichlorophenyl)urea, melting point 250° C.

N-(2,6-dichlorobenzoyl)-N'-(methyl)-N'-(3,4-dichlorophenyl)urea, melting point 178° C.

N-(2,6-dichlorobenzoyl)-N'-(ethyl)-N'-(3,4-dichlorophenyl)urea, melting point 154° C.

N-(2,6-dichlorobenzoyl)-N'-(methyl)-N'-(4-t.butylphenyl)urea, melting point 158° C.

N-(2,6-dichlorobenzoyl)-N'-(methyl)-(4-bromophenyl)urea, melting point 182° C.

N-(2,6-dichlorobenzoyl)-N'-(ethyl)-N'-(4-bromophenyl)urea, melting point 148° C.

N-(2,6-dichlorobenzoyl)-N'-(ethyl)-N'-4-isopropylphenyl)urea, melting point 135° C.

N-(2,6-dichlorobenzoyl)-N'-(ethyl)-N'-(4-n.butylphenyl)urea, melting point 130° C.

N-(2,6-dichlorobenzoyl)-N'-(methyl)-N'-(4-chlorophenyl)urea, melting point 176° C.

N-(2,6-dichlorobenzoyl)-N'-(ethyl)-N'-(4-chlorophenyl)urea, melting point 146° C.

N-(2,6-dichlorobenzoyl)-N'-(ethyl)-N'-(4-t.butylphenyl)urea, melting point 130° C.

N-(2,6-dichlorobenzoyl)-N'-(methyl)-N'-(4-nitrophenyl)urea, melting point 195° C.

3-(2,6-dichlorobenzoyl)-1-(4-chlorophenyl)-parabanesaure, melting point 157° C.

N-(2,6-dichlorobenzoyl)-N'-(2,4,5-trichlorophenyl)urea, melting point 270° C.

N-(2,6-dichlorobenzoyl)-N'-(phenyl)urea, melting point 195° C.

N-(2,6-dichlorobenzoyl)-N'-(4-nitrophenyl)urea, melting point 256° C.

N-(2,6-difluorobenzoyl)-N'-(4-trifluoromethylphenyl)urea, melting point 255° C.

N-(2,6-difluorobenzoyl)-N'-(4-n.butylphenyl)urea, melting point 193° C.

N-(2,6-difluorobenzoyl)-N'-(4-t.butylphenyl)urea, melting point 214° C.

N-(2,6-difluorobenzoyl)-N'-(4-isopropylphenyl)urea, melting point 196° C.

N-(2,6-difluorobenzoyl)-N'-(3-fluoro-4-iodobenzyl)urea, melting point 253° C.

N-(2,6-difluorobenzoyl)-N'-(3-fluoro-4-chlorophenyl)urea, melting point 237° C.

N-(2,6-difluorobenzoyl)-N'-(3-trifluoromethylphenyl)urea, melting point 201° C.

N-(2,6-difluorobenzoyl)-N'-(4-isobutylphenyl)-N'-(methyl)urea, melting point 92° C.

N-(2,6-difluorobenzoyl)-N'-(4-chlorophenyl)urea, melting point 239° C.

N-(2,6-difluorobenzoyl)-N'-(4-bromophenyl)urea, melting point 247° C.

N-(2,6-difluorobenzoyl)-N'-(4-fluorophenyl)urea, melting point 211° C.

N-(2,6-difluorobenzoyl)-N'-(4-thiomethylphenyl)urea, melting point 202° C.

N-(2,6-difluorbenzoyl)-N'-(methyl)-N'-(4-chlorphenyl)urea, melting point 124° C.

N-(2,6-difluorbenzoyl)-N-(methoxymethyl)-N'-(3,4-dichlorophenyl)urea, melting point 145° C.

To illustrate the high activity of these substances we will mention that nearly all the above individually enumerated compounds according to the invention when used in a concentration of 10 ppm (parts per million) result in a 90–100% kill of larvae of *Pieris brassica*. Many of the above substances even produce a 90–100% kill in a concentration of 3 ppm. Some compounds, such as N-(2,6-dichlorobenzoyl)-N'-(3,4-dichlorophenyl)urea,
N-(2,6-dichlorobenzoyl)-N'-(4-chlorophenyl)urea,
N-(2,6-dichlorobenzoyl)-N'-(4-butylphenyl)urea,
N-(2,6-dichlorobenzoyl)-N'-(4-bromophenyl)urea,
N-(2,6-dichlorobenzoyl)-N'-(4-iodophenyl)urea,
N-(2,6-dichlorobenzoyl)-N'-(3-fluoro-4-chlorophenyl)urea,
N-(2,6-dichlorobenzoyl)-N'-(4-trifluoromethylphenyl)urea,
N-(2,6-dichlorobenzoyl)-N'-(3-fluoro-4-bromophenyl)urea,
N-(2,6-dichlorobenzoyl)-N'-(2-fluoro-4-iodophenyl)urea,
N-(2,6-difluorobenzoyl)-N'-(3,4-dichlorophenyl)urea, N-(2,6-dichlorobenzoyl)-N'-(ethyl)-N'-(4-bromophenyl)urea,
N-(2,6-difluorobenzoyl)-N'-(4-trifluoromethylphenyl)urea,
N-(2,6-difluorobenzoyl)-N'-(4-n butylphenyl)urea,
N-(2,6-difluorobenzoyl)-N'-(4-t.butylphenyl)urea,
N-(2,6-difluorobenzoyl)-N'-(4-isopropylphenyl)urea,
N-(2,6-difluorobenzoyl)-N'-(3-fluoro-4-iodophenyl)urea,
N-(2,6-difluorobenzoyl)-N'-(3-fluoro-4-chlorophenyl)urea,
N-(2,6-difluorobenzoyl)-N'-(3-trifluoromethylphenyl)urea,
N-(2,6-difluorobenzoyl)-N'-(4-isobutylphenyl)-N'-(methyl)urea,
N-(2,6-difluorobenzoyl)-N'-(4-chlorophenyl)urea,
N-(2,6-difluorobenzoyl)-N'-(4-bromophenyl)urea,
N-(2,6-difluorobenzoyl)-N'-(4-fluorophenyl)urea,
cause a 90–100% kill of *Pieris brassica* larvae in a dosage concentration of from 0.1–1 ppm. This exceptionally high activity is of prime importance and is to be considered as extremely surprising.

A very satisfactory biocidal activity against larvae of the yellow fever mosquito (*Aedes aegypti*), i.e. a sufficiently killing effect in a concentration of 0.1 ppm or even less, has been found inter alia in respect of the following compounds:
N-(2,6-dichlorobenzoyl)-N'-(3,4-dichlorophenyl)urea, melting point 238° C.
N-(2,6-dichlorobenzoyl)-N'-(4-dichlorophenyl)-urea, melting point 236° C.
N-(2,6-dichlorobenzoyl)-N'-(2,4-dichlorophenyl)urea, melting point 238° C.
N-(2,6-dichlorobenzoyl)-N'-(4-cyclopropylphenyl)urea, melting point 208° C.
N-(2,6-dichlorobenzoyl)-N'-(4-methylphenyl)urea, melting point 242° C.
N-(2,6-dichlorobenzoyl)-N'-(fluorophenyl)urea, melting point 212° C.
N-(2,6-dichlorobenzoyl)-N'-(3-trifluoromethylphenyl)urea, melting point 230° C.
N-(2,6-dichlorobenzoyl)-N'-(2,5-difluoro-4-bromophenyl)urea, melting point 270° C.
N-(2,6-dichlorobenzoyl)-N'-(3-fluoro-4-chlorophenyl)urea, melting point 225° C.
N-(2,6-dichlorobenzoyl)-N'-(4-phenylphenyl)urea, melting point 260° C.
N-(2,6-dichlorobenzoyl)-N'-(4-cyanophenyl)urea, melting point 248° C.
N-(2,6-dichlorobenzoyl)-N'-(4-pentylthiophenyl)urea, melting point 130° C.
N-(2,6-dichlorobenzoyl)-N'-(3-fluoro-4-iodophenyl)urea, melting point 220° C.
N-(2,6-dichlorobenzoyl)-N'-(2-fluoro-4-iodophenyl)urea, melting point 256° C.
N-(2,6-dichlorobenzoyl)-N'-(4-n.propylphenyl)urea, melting point 194° C.
N-(2,6-dichlorobenzoyl)-N'-(4-sec.butylphenyl)urea, melting point 168° C.
N-(2,6-dichlorobenzoyl)-N'-(4-isobutylphenyl)urea, melting point 215° C.
N-(2,6-dichlorobenzoyl)-N'-(4-ethylphenyl)urea, melting point 228° C.
N-(2,6-dichlorobenzoyl)-N'-(4-n.dodecylphenyl)urea, melting point 117° C.
N-(2,6-dichlorobenzoyl)-N'-(4-benzylphenyl)urea, melting point 207° C.
N-(2,6-dichlorobenzoyl)-N'-(4-trifluoromethylphenyl)urea, melting point 214° C.
N-(2-chlorobenzoyl)-N'-(3,4-dichlorophenyl)urea, melting point 209° C.
N-(2-bromobenzoyl)-N'-(3,4-dichlorophenyl)urea, melting point 217° C.
N-(2,6-dibromobenzoyl)-N'-(3,4-dichlorophenyl)urea, melting point 250° C.
N-(2,6-dichlorobenzoyl)-N'-(methyl)-N'-(3,4-dichlorophenyl)urea, melting point 178° C.
N-(2,6-dichlorobenzoyl)-N-(methyl)-N'-(3,4-dichlorophenyl)urea, melting point 182° C.
N-(2,6-dichlorobenzoyl)-N'-(ethyl)-N'-(3,4-dichlorophenyl)urea, melting point 153° C.
N-(2,6-dichlorobenzoyl)-N'-(methyl)-N'-(4-bromophenyl)urea, melting point 182° C.
N-(2,6-dichlorobenzoyl)-N'-(ethyl)-N'-(4-bromophenyl)urea, melting point 148° C.
N-(2,6-dichlorobenzoyl)-N-(methyl)-N'-(4-chlorophenyl)urea, melting point 124° C.
N-(2,6-dichlorobenzoyl)-N-(methoxymethyl)-N'-(4-chlorophenyl)urea, melting point 122° C.
N-(2,6-dichlorobenzoyl)-N-(methoxymethyl)-N'-(3,4-dichlorophenyl)urea, melting point 145° C.
3-(2,6-dichlorobenzoyl)-1-(4-chlorophenyl)parabanic acid, melting point 157° C.
N-(2,6-dichlorothiobenzoyl)-N'-(3,4-dichlorophenyl)urea, melting point 168° C.
N-(2,6-dichlorothiobenzoyl)-N'-(3,4-dichlorophenyl)thiourea, melting point 169° C.

Examples of other active substances according to the invention are:
N-(2,6-dichlorobenzoyl)-N'-(3-chlorophenyl)urea, melting point 237° C.
N-(2,6-dichlorobenzoyl)-N'-(2,3-dimethylphenyl)urea, melting point 238° C.
N-(2,6-dichlorobenzoyl)-N'-(5,6,7,8-tetrahydro-2-naphthyl)urea, melting point 196° C.
N-(2,6-dichlorobenzoyl)-N'-(3,4-dioxymethylenephenyl)urea, melting point 242° C.
N-(2,6-dichlorobenzoyl)-N'-(4-dichlorocyclopropylphenyl)urea, melting point 245° C.
N-(2,6-dichlorobenzoyl)-N'-(4-methylsulphenyl)urea, melting point 222° C.
N-(2,6-dichlorobenzoyl)-N'-(3-bromo-4-chlorophenyl)urea, melting point 254° C.
N-(2,6-dichlorobenzoyl)-N'-[4-(p-chlorophenoxy)phenyl]urea, melting point 205° C.
N-(2,6-dichlorobenzoyl)-N'-(3,5-dicyanophenyl)urea, melting point 255° C.
N-(2,6-dichlorobenzoyl)-N'-(3,4,5-trichlorophenyl)urea, melting point 270° C.
N-(2,6-dichlorobenzoyl)-N'-(3-chloro-4-methylphenyl)urea, melting point 228° C.
N-(2,6-dichlorobenzoyl)-N'-(4-acetylphenyl)urea, melting point 212° C.
N-(2,6-dichlorobenzoyl)-N'-(3-chloro-4-thiomethylphenyl)urea, melting point 242° C.
N-(2,6-dichlorobenzoyl)-N'-(2,5-difluorophenyl)urea, melting point 225° C.
N-(2,6-dichlorobenzoyl)-N'-(4-thiomethylphenyl)urea, melting point 216° C.
N-(2,6-dichlorobenzoyl)-N'-(3-chloro-4-nitrophenyl)urea, melting point 300° C.
N-(2,6-dichlorobenzoyl)-N'-(3,4-dimethylphenyl)urea, melting point 202° C.
N-(2,6-dichlorobenzoyl)-N'-(2-fluorophenyl)urea, melting point 205° C.

N-(2,6-dichlorobenzoyl)-N'-(3-fluorophenyl)urea, melting point 222° C.
N-(2,6-dichlorobenzoyl)-N'-(4-dimethylaminosulphonylphenyl)urea, melting point 232° C.
N-(2,6-dichlorobenzoyl)-N'-(3-nitro-4-methylphenyl)urea, melting point 256° C.
N-(2,6-dichlorobenzoyl)-N'-(3-methoxyphenyl)urea, melting point 194° C.
N-(2,6-dichlorobenzoyl)-N'-(4-phenylthiophenyl)urea, melting point 196° C.
N-(2,6-dichlorobenzoyl)-N'-(4-benzoylphenyl)urea, melting point 198° C.
N-(2,6-dichlorobenzoyl)-N'-(3-dichlorocyclopropylphenyl)urea, melting point 220° C.
N-(2,6-dichlorobenzoyl)-N'-(4-pentylsulphonylphenyl)urea, melting point 167° C.
N-(2,6-dichlorobenzoyl)-n'-(4-n.octylphenyl)urea, melting point 124° C.
N-(2,6-dichlorobenzoyl)-N'-(4-methylthiomethylphenyl)urea, melting point 214° C.
N-(2-methoxybenzoyl)N'-(3,4-dichlorophenyl)urea, melting point 170° C.
N-(2,6-dichlorobenzoyl)-N'-(methyl)-N'-(phenyl)urea, melting point 138° C.
N-(2,6-dichlorobenzoyl)-N'-(hydroxy)-N'-(2,4,5-trichlorophenyl)urea, melting point 220° C.
N-(2,6-dichlorobenzoyl)-N'-(pentyl)-N'-(3,4-dichlorophenyl)urea, melting point 160° C.
N-(2,6-dichlorobenzoyl)-N'-(acetyl)-N'-(3,4-dichlorophenyl)urea, melting point 180° C.
N-(2,6-dichlorobenzoyl)-N'-(ethoxycarbonyl)-N'-(3,4-dichlorophenyl)urea, melting point 185° C.
N-(2,6-dichlorobenzoyl)-N'-(pentyl)-N'-(4-bromophenyl)urea, melting point 145° C.
N-(2,6-dichlorobenzoyl)-N'-(methyl)-N'-(4-isopropylphenyl)urea, melting point 124° C.
N-(2,6-dichlorobenzoyl)-N'-(pentyl)-N'-(4-chlorophenyl)urea, melting point 138° C.
N-(2,6-dichlorobenzoyl)-N'-(ethyl)-N'-(4-n.propylphenyl)urea, melting point 110° C.
N-(2,6-dichlorobenzoyl)-N'-(ethyl)-N'-(4-sec.butylphenyl)urea, melting point 118° C.
N-(2,6-dichlorobenzoyl)-N'-(ethyl-N'-(4-isobutylphenyl)urea, melting point 154° C.
N-(2,6-dichlorobenzoyl)-N'-(pentyl)-N'-(4-t.butylphenyl)urea, melting point 82° C.
N-(2,6-dichlorobenzoyl)-N'-(benzyl)-N'-(4-chlorophenyl)urea, melting point 188° C.
N-(2,6-dichlorobenzoyl)-N'-(methyl)-N'-(4-n.butylphenyl)urea, melting point 152° C.
N-(2,6-dichlorobenzoyl)-N'-(n.pentyl)-N'-(4-n.butylphenyl)urea, melting point 104° C.
N-(2,6-dichlorobenzoyl)-N-(methyl)-N'-(methyl)-N'-(3,4-dichlorophenyl)urea, melting point 130° C.
N-(2,6-dichlorobenzoyl)-N'-(methyl)-N'-(4-sec.butyl-phenyl)urea, melting point 131° C.
N-(2,6-dichlorobenzoyl)-N'-(methyl)-N'-(4-isobutylphenyl)urea, melting point 163° C.
N-(2,6-dichlorobenzoyl)-N'-(methyl)-N'-(4-n.propylphenyl)urea, melting point 146° C.
3-(2,6-dichlorobenzoyl)-1-(p-chlorophenyl)hydantoine urea, melting point 183° C.
N-(2,6-dichlorobenzoyl)-N'-(pyridyl-2)urea, melting point 216° C.
N-(2,6-dichlorobenzoyl)-N'-(4-chloropyridyl-2)urea, melting point 197° C.
N-(2,6-dichlorobenzoyl)-N'-(3,4-dichlorophenyl)thiourea, melting point 240° C.

By virtue of their activity the substances according to the invention may be used to control insects found in agriculture and horticulture, such as caterpillars and beetles, and to preserve textile fabrics, such as, for example, to protect furs, carpets and textile stocks against attack by, for example, moths and carpet beetles.

For practical use the compounds according to the invention are worked up into preparations. In these preparations the active substance is mixed with a solid carrier material or dissolved or dispersed in a liquid carrier material, if desired combined with adjuvants, such as surface-active substances and stabilizers.

Examples of preparations according to the invention are aqueous solutions and dispersions, oil solutions and oil dispersions, pastes, dusts, wettable powders, miscible oils, granules, invert emulsions, aerosol preparations and fumigating candles.

Wettable powders, pastes and miscible oils are preparations in concentrated form which are diluted with water before or during use.

The invert emulsions are mainly used in air application, large surface areas being treated with a comparatively small amount of preparation. A short time before, or even during, the spraying the invert emulsion may be prepared in the spraying apparatus by emulsifying water in an oil solution or an oil dispersion of the active substance. Some forms of preparations will now be described in greater detail by way of example.

Granular preparations are produced by, for example, taking up the active substance in a solvent, after which granular carrier material, such as porous granules (for example pumice and attaclay), mineral non-porous granules (sand or ground marl) and organic granules (for example dried coffee grounds and cut tobacco stems), is impregnated with the solution, as the case may be in the presence of a binder.

A granular may also be produced by compressing the active substance together with powdered minerals in the presence of lubricants and binders and disintegrating and straining the comprimate to the desired grain size.

Dusts are obtainable by intimately mixing the active substance with an inert solid carrier material in a concentration of, for example, from 1-50% by weight. Examples of suitable solid carrier materials are talc, kaolin, pipeclay, diatom earth, dolomite, gypsum, chalk, bentonite, attapulgite and colloidal $SiO_2$ or mixtures of those and similar substances. Alternatively organic carrier materials may be used such as, for example, ground walnut shells.

Wettable powders are produced by mixing from 10-80 parts by weight of a solid inert carrier such as, for example, one of the aforementioned carrier materials with from 10-80 parts by weight of the active substance, from 1-5 parts by weight of a dispersing agent such, for example, as the lignin sulfonate or alkyl naphthalene sulfonates known for this purpose, and preferably also with from 0.5-5 parts by weight of a wetting agent such as one of the fatty alcohol sulfates, alkylaryl sulfonates or fatty acid condensation products, for example those known under the trade mark Igepon.

To produce miscible oils the active substance is dissolved or finely divided in a suitable solvent which preferably is poorly miscible with water after which an emulsifier is added to the solution. Examples of suitable solvents are xylene, toluene, high-aromatic pertroleum distillates, for example solvent naphtha, distilled tar oil and mixtures of these liquids. Examples of emulsifiers are alkylphenoxypolyglycol ethers, polyoxyethylene sorbitan esters of fatty acids or polyoxyethylene sorbitol esters of fatty acids. In these miscible oils the concentration of the active compound is not restricted within narrow limits and may vary between, say, 2% and 50% by weight. In addition to being a miscible oil the liquid and highly concentrated primary composition may be a solution of the active substance in a satisfactorily water-miscible liquid, for example acetone, to which solution a dispersing agent and possibly a wetting agent has or have been added. Dilution with water shortly before or during the spraying operation results in an aqueous dispersion of the active substance.

An aerosol preparation according to the invention is obtained in the usual manner by incorporating the active substance, as the case may be in a solvent, in a volatile liquid suitable for use as a propellant, for example the mixture of chlorine and fluorine derivatives of methane and ethane commercially available under the trademark "Freon".

Fumigating candles or fumigating powders, i.e. preparations which when burning are capable of emitting a pesticidal smoke, are obtained by taking up the active substance in a combustible mixture which may contain, for example, a sugar or a wood, preferably in ground form, as a fuel, a substance to maintain combustion such, for example, as ammonium nitrate or potassium chlorate, and furthermore a substance to retard the combustion, for example kaolin, bentonite and/or colloidal silicic acid.

Besides the above-mentioned ingredients the preparations according to the invention may contain other substances known for use in preparations of this type.

For example, a lubricant such as calcium stearate or magnesium stearate may be added to a wettable powder or to a mixture to be granulated. Also, "adhesives" such as polyvinylalcoholcellulose derivatives or other colloidal materials, such as casein, may be added to improve the adherence of the pesticide to the surface to be protected.

The preparations according to the invention may also include other, known pesticidal compounds. This broadens the spectrum of activity of the preparation and may produce synergism.

The following known insecticidal, fungicidal and acaricidal compounds are suitable for use in such a combined preparation:

Insecticides such as:

1. chlorinated hydrocarbons, for 2,2-bis(p-chlorophenyl)-1,1,1-trichloroethane and hexachloro-epoxyoctahydrodimethanonaphthalene;

2. carbamates, for example N-methyl-1-naphthylcarbamate;

3. dinitrophenols, for example 2-methyl-4,6-dinitrophenyl and 2-(2-butyl)-4,6-dinitrophenyl-3,3-dimethylacrylate;

4. organic phosphor compounds, such as dimethyl-2-methoxy-carbonyl-1-methylvinyl phosphate, O,O-diethyl-O-p.nitrophenylphosphorthionate, N-monomethylamide of O,O-dimethyl-dithiophosphoryl acetic acid.

Acaricides such as:

5. diphenylsulfides, for example p-chlorobenzyl and p-chlorophenyl sulfide and 2,4,4',5-tetrachlorodiphenylsulfide;

6. diphenylsulfonates, for example p-chlorophenylbenzene sulfonate;

7. methylcarbinols, for example 4,4-dichloro-a-trichloromethylbenzhydrol;

8. quinoxaline compounds, such as methylquinoxaline dithiocarbonate.

Fungicides such as:

9. organic mercury compounds, for example phenyl mercury acetate and methyl mercury cyanoguanide;

10. organic tin compounds, for example triphenyl tin hydroxide and triphenyl tin acetate;

11. alkylene bisdithiocarbamates, for example zinc ethylene bisdithiocarbamate and manganese ethylene bisdithiocarbamate;

12. and further:

2,4-dinitro-6-(2-octylphenylcrotonate),
1-[bis(dimethylamino)phosphoryl]-3-phenyl-5-amino-1,2,4-triazole, 6-methyl-quinoxaline-2,3-dithiocarbonate,
1,4-dithiocanthraquinone-2,3-dicarbonitrile,
N-trichloromethylthiophthalimide,
N-trichloromethylthiotetrahydrophthalimide,
N-(1,1,2,2-tetrachloro-ethylthio)-tetrahydrophthalimide,
N-dichlorofluoromethylthio-N-phenyl-N'-dimethylsulfonyldiamide and tetrachloroisophthalonitrile.

The dosage desirable for practical use of the preparation according to the invention will naturally depend on various factors, such as the field of use, the active substance chosen, the form of preparation, the nature and the degree of the infection.

For agricultural use in general a dosage corresponding to from 10–5,000 g of active substance per hectare will yield the desired effect.

The compounds according to the invention are new substances which may be produced by methods known for the production of similar substances or by analogous methods. For example, the substances may be produced by (a) reacting a compound of the formula

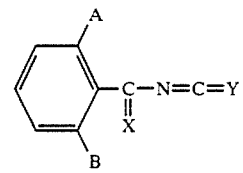

where A, B, X and Y have the aforementioned meanings, with a compound of the formula

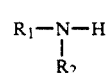

where $R_1$ and $R_2$ have the aforementioned meanings, so as to obtain a compound of the formula

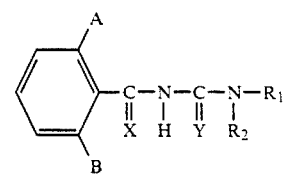

(b) reacting a compound of the formula

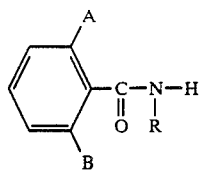

where A, B and R have the aforementioned meanings, with a compound of the formula

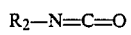

R$_2$—N=C=O where R$_2$ has the aforementioned meaning, so as to obtain a compound of the formula

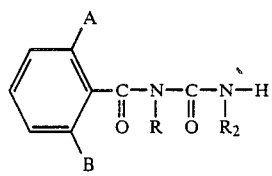

(c) reacting a compound of the formula

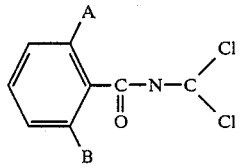

where A and B have the aforementioned meanings, with a compound of the formula

R$_2$—NH$_2$ where R$_2$ has the aforementioned meaning, and by subsequently hydrolising the resulting reaction product, which may be show by the formula

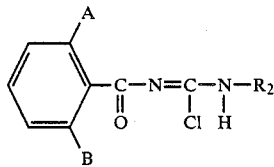

so as to obtain a final product of the formula

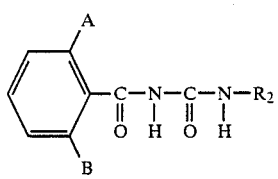

(d) reacting a compound of the formula

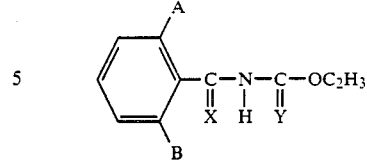

where A and B have the aforementioned meanings, with a compound of the formula

R$_2$—NH$_2$ where R$_2$ has the aforementioned meaning, so as to obtain a compound of the formula

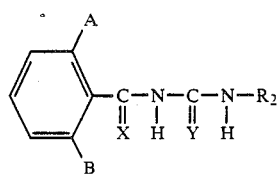

(e) reacting a compound of the formula

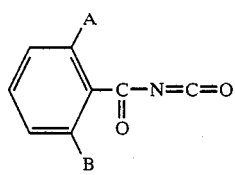

where A and B have the aforementioned meanings, with a compound of the formula

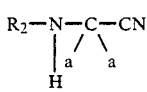

where R$_2$ has the aforementioned meanings and a represents a hydrogen atom or an alkyl group, whilst furthermore the substituents a together with the carbon atom bound to them may form a cycloalkyl group containing from 3-6 carbon atoms, and subsequently acidifying the resulting reaction product, which may be represented by the formula

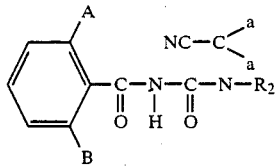

so as to obtain a compound of the formula

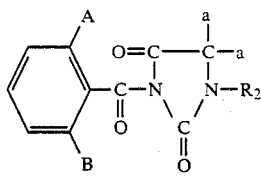

(f) reacting a compound of the formula

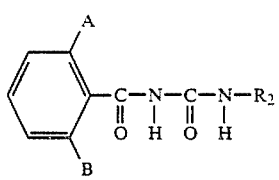

where A, B and R$_2$ have the aforementioned meanings, with oxalylchloride, so as to obtain a compound of the formula

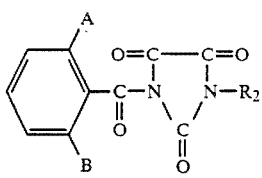

(g) reacting a compound of the formula

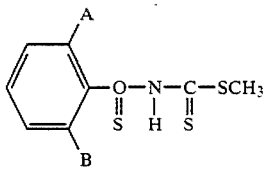

where A and B have the aforementioned meanings, with a compound of the formula

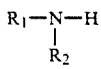

where R$_1$ and R$_2$ have the aforementioned meanings, so as to obtain a compound of the formula

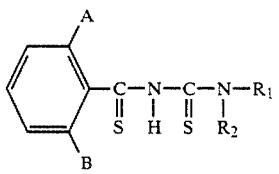

(h) reacting a compound of the formula

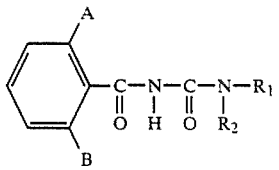

where A, B, R$_1$ and R$_2$ have the aforementioned meanings, with a compound of the formula

where R$_{10}$ is an alkyl group or an alkoxymethyl group and Hal is a halogen atom, so as to obtain a compound of the formula

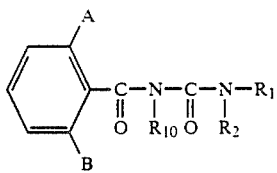

(i) reacting a compound of the formula

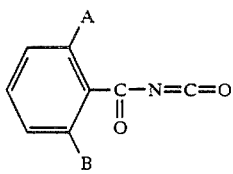

where A and B have the aforementioned meanings, with a compound of the formula

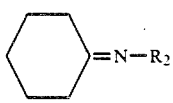

where R$_2$ has the aforementioned meaning, so as to obtain a compound of the formula

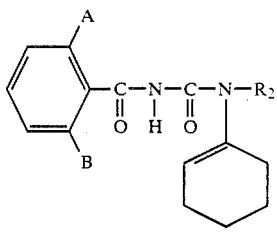

(k) reacting a compound of the formula

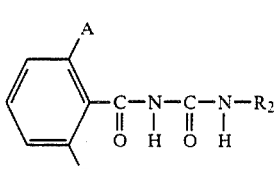

where A, B and R$_2$ have the aforementioned meanings, with a compound of the formula Cl—CH$_2$—O—CH$_2$—Cl so as to obtain a compound of the formula

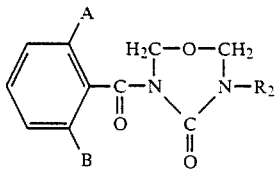

Amongst these methods the method a is preferably used. The efficiency of the method a is satisfactory.

The method a is carried out in the presence of a solvent at a reaction temperature which may vary from 0° C. to the boiling point of the solvent used. Examples of suitable solvents are aromatic hydrocarbons, such as benzene, chlorinated hydrocarbons, such as chloroform, methylene chloride or ethylene chloride, or another inert solvent, such as acetonitrile.

The starting product for the method a is obtainable by treating the corresponding benzamide with oxalylchloride in the presence of a solvent such as a chlorinated hydrocarbon, for example, methylene chloride.

Examples of other methods of synthesizing the starting products for the process a are:

I reacting a compound of the formula

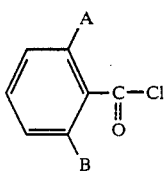

with ammoniumhodanide, so as to obtain a compound of the formula

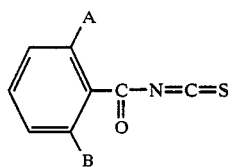

II heating a solution of a compound of the formula

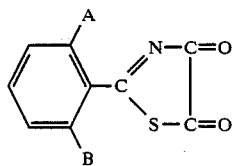

so as to obtain a substance of the formula

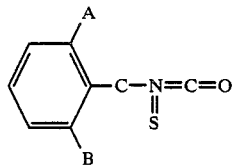

The method b is preferably carried out in a reaction medium containing pyridine and sodium. The reaction is effected at an elevated temperature, for example 100° C.

The method c is performed in the presence of a base capable of binding the HCl evolved. Examples of suitable bases are triethylamine and 3,4-dichloroaniline. The condensation reaction is carried out in the presence of a solvent, such as benzene, toluene, chlorobenzene, methylene chloride, chloroform or carbontetrachloride. The reaction temperature may vary between 0° C. and the boiling point of the solvent used. The hydrolysis of the intermediate product of the method c may simply be effected. For example the intermediate product may be exposed to moist air or agitated with water.

The reaction described in the method d takes place in the presence of a solvent. Examples of suitable solvents are xylene, toluene, chlorobenzene and other similar inert solvents having a boiling point higher than about 100° C. The reaction is carried out at a temperature which is about equal to the boiling point of the solvent used. The reaction time is several hours.

In the method e the first step is effected in the presence of a solvent such as dry benzene. During the reaction, the reaction mixture is slightly cooled. The intermediate product obtained in the first step is acidified by a treatment with, for example, a solution of an inorganic acid in acetic acid. Suitable inorganic acids are HBr, $H_2SO_4$, HCl and the like.

The reaction with oxalylchloride according to the method f is performed in the presence of a solvent. Suitable solvents are aromatic hydrocarbons, such as benzene and toluene, and chlorinated hydrocarbons, such as chloroform, carbon tetrachloride and dichloroethane. The reaction is carried out an elevated temperature, for example at the boiling point of the solvent used.

The reaction according to the method g proceeds in the presence of a solvent, such as a hydrocarbon, for example toluene, and at a reaction temperature which may vary between room temperature and the boiling point of the solvent used.

The process described under the heading h is performed in the presence of a solvent and a basic substance. A suitable reaction medium is, for example, dimethylformamide containing an alkalihydroxide.

The reaction according to the method i is performed in the presence of a solvent, such as an ether, for example, diethyl ether. The reaction temperature is preferably about equal to room temperature.

The reaction conditions in performing the method k are the same as those described in the method h.

The invention will now be described more fully with reference to the following Examples.

1. Production of N-(2,6-dichlorobenzoyl)-N'-(3,4-dichlorophenyl)-urea.

9.5 g of 2,6-dichlorobenzamide and 10.34 g of 3,4-dichlorophenylisocyanate in 25 ml of pyridine to which 1 g of sodium has been added are heated on a steam bath (100° C.+) for 24 hours. The reaction mixture is poured on ice which contains concentrated hydrochloric acid and the solid precipitate is thoroughly washed with successively water and alcohol. The substance is recristallized from acetonitrile. Melting point 232° C.

2. Production of N-(2,6-dichlorobenzoyl)-N'-(3,4-dichlorophenyl)-urea.

(a) Production of 2,6-dichlorobenzoylisocyanate.

95 g of 2,6-dichlorobenzamide are suspended in from 250 to 300 ml of dry methylene chloride. After the addition of 56 ml of oxalyl chloride the mixture is slowly heated to boiling point, at which temperature the starting material rapidly dissolves with a strong evolution of hydrochloric acid. After boiling for from 15–18 hours the mixture is concentrated by evaporation in a vacuum. The resulting 2,6-dichlorobenzoylisocyanide is used for the next reaction step without further purification.

(b) Production of N-(2,6-dichlorobenzoyl)-N'-(3,4-dichlorophenyl)-urea.

35 g of 2,6-dichlorobenzoylisocyanate in 100 ml of dry benzene are added drop by drop, with stirring and cooling, to a solution of 24.3 g of 3,4-dichloroaniline in 200 ml of dry benzene. Much heat is evolved and a precipitate is formed which is drawn off while hot and then is washed with hot benzene. The resulting N-(2,6-dichlorobenzoyl)-N'-(3,4-dichlorophenyl)-urea is pure, as is shown by thin layer chromatography (with ethylacetate as the solvent). If desired, the product may be recrystallized from acetonitrile. Melting point 238° K.

3. Production of N-(2,6-dichlorothiobenzoyl)-N'-(3,4-dichlorophenyl)-urea.

26.0 g of 2-(2,6-dichlorophenyl)-thiazoline-4,5-dione are suspended in 250 ml of dry toluene and heated to 90° C. while stirring. Gas is evolved and a violet solution is obtained, to which is added 16.2 g of 3,4-dichloroaniline dissolved in 30 ml of toluene. After stirring for 15 minutes the solution is cooled and the precipitate obtained is drawn off. Yield 20.1 g. Melting point 168° C.

4. Production of N-(2,6-dichlorobenzoyl)-N'-(3,4-dichlorophenyl)-thiourea.

10.5 g of 2.6-dichlorobenzoylchloride are added drop by drop with stirring to a solution of 3.8 g of ammonium rhodanide in 15 ml of acetone. After boiling for 15 minutes the reaction mixture is added drop by drop to a solution of 8.1 g of 3,4-dichloroaniline in 15 ml of acetone. After stirring for 30 minutes the reaction mixture is poured in water and extracted with ether. The ethereal solution is dried and concentrated by evaporation and the residue is taken up in benzene. After working up and decrystallizing from benzene 1.3 g of the superscribed substance is obtained. Melting point 240° C.

5. Production of N-(2,6-dichlorothiobenzoyl)-N'-(3,4-dichlorophenyl)-thiourea.

3.0 g of N-(2,6-dichlorothiobenzoyl)-S-methyldithiocarbamate and 1.6 g of 3,4-dichloroaniline are dissolved in 25 ml of toluene and subsequently heated while refluxing for 5 hours. The resulting yellow precipitate is worked up in the usual manner. Yield 2.1 g. Melting point 168°-170° C.

6. Production of N-(2,6-dichlorobenzoyl)-N-(methyl)-N'-(4-chlorophenyl)-urea.

10.3 g of N-(2,6-dichlorobenzoyl)-N'-(4-chlorophenyl)-urea and 1.88 g of powdered potassium hydroxide (90%) are dissolved 40 ml of dimethyl formamide, after which 4.7 g of methyl iodide are added drop by drop to the clear solution. The resulting reaction is exothermic. After stirring for two hours the solution is diluted with ice water and the solid substance is isolated. Yield 10.3 g. Melting point 124°-126° C. In a completely similar manner but using methoxymethylchloride instead of methyliodide, N-(2,6-dichlorobenzoyl)-N-(methoxymethyl)-N'-(4-chlorophenyl)-urea is produced. Melting point 121.5°-122.5° C.

7. Production of 3-p-chlorophenyl-5-(2,6-dichlorobenzoyl)-2,3,5,6-tetrahydro-4H-1,3,5-oxadiazinone-4.

6.5 g of N-(2,6-dichlorobenzoyl)-N'-(4-chlorophenyl) urea and 1.3 g of 90% powdered potassium hydroxide are dissolved in 25 ml of dimethylformamide, after which 2.18 g of dichlorodimethylether are added to the solution. After stirring for two hours at 0° C., another portion of 1.3 g of 90% powdered potassium hydroxide is added, after which the mixture is stirred for 24 hours at room temperature. After dilution with ice water the obtained solid substance is isolated and chromatographed. Yield 2.1 g. Melting point 164°-168° C.

8. Production of N-(2,6-dichlorobenzoyl)-N'-(4-chlorophenyl)-N'-(cyclohexenyl-1)-urea.

3.1 g of 1-(4-chloroaniline)-cyclohexene are dissolved in 50 ml of absolute ether and to this solution is added a solution of 3.25 g of 2,6-dichlorobenzoylisocyanate in 10 ml of absolute ether. After a short time a precipitate is produced which is drawn off and washed with ether. Yield 5.1 g. Melting point 156°-158° C.

9. Production of N-(2,6-dichlorobenzoyl)-N'-(3,4-dichlorophenyl)-urea.

A solution of 1.62 g of 3,4-dichloroaniline and 1.01 g of triethylamine in 20 ml of benzene was added drop by drop to a solution of 2.71 g of 2,6-dichlorobenzoylisocyaninedichloride in 25 ml of benzene while stirring at 20° C. There is a slight rise in temperature and a white precipitate is produced. After stirring for two hours the white substance is drawn off and the filtrate is exposed to moist air. After 24 hours almost perfect crystals are produced, which are isolated. Melting point 236° C. Yield 1.3 g.

10. Production of N-(2,6-dichlorobenzoyl)-N'-(3,4-dichlorophenyl)-urea.

2.62 of N-(2,6-diichlorobenzoyl)-ethylurethane and 1.62 g of 3,4-dichloroaniline are added to 10 ml of xylene and heated at boiling point for two hours, the alcohol formed being distilled off. After cooling, the crystals formed are filtered off. Yield 3.4 g. Melting point 236° C.

11. Production of 3-(2,6-dichlorobenzoyl)-1-(p-chlorophenyl)-hydantoin.

(a) Preparation of N-(2,6-dichlorobenzoyl)-N'-(cyanomethyl)-N'-(p-chlorophenyl)-urea.

16.0 g of 2,6-dichlorobenzoylisocyanate are added in small portions to a solution of 11.66 g of p-chloroanilino-acetonitrile in 100 ml of dry benzene with moderate cooling. After some time a substance crystallizes out, which after about 12 hours is drawn off and washed with benzene. After drying the weight is 25.25 g, i.e. 93.7% the melting point being 185° C. with spontaneous decomposition on the Kofler heating bench. Thin-lyer chromatography (solvent either ethylacetate or chloroform) shows that the substance is pure, however, if desired, it may be recrystallized from 250 ml of benzene with a yield of 80%.

(b) Preparation of 3-(2,6-dichlorobenzoyl)-1-(p-chlorophenyl)-hydantoin.

25 g of the substance prepared by the method described in 11a were stirred at room temperature in 150 mL of about 15% HBr solution in acetic acid, the substance dissolving almost completely with the rapid formation of a thick precipitate. After being heated (at 40° C.) for a short time and being allowed to stand for some hours, the suspension is poured in half a liter of water, drawn off, washed with water and dried. Yield 24 g. Melting point 176°-180° C.

12. Production of 3-(2,6-dichlorobenzoyl)-1-(p-chlorophenyl)-parabanic acid.

10.3 g of N-(2,6-dichlorobenzoyl)-N'-(p-chlorophenyl)-urea are boiled in 100 ml of dry 1,2-dichloroethane containing 3 ml of oxalylchloride for 24 hours. The urea dissolves with the evolution of hydrochloric acid. After concentration by evaporation and after the addition of 25 ml of ligroin the residue becomes crystalline. The substance may be recrystallized from 30 mls of benzene. Melting point 157° C. Yield 8 g.

It should be noted that the substances enumerated in the specification were produced in a manner which is entirely analogous to the methods illustrated in the above Examples. In producing the large number of compounds according to the invention especially the above described method (a), which is illustrated by the Examples 2, 3, 4 and 5, is frequently used.

13. From the substances enumerated in this specification wettable powders have been prepared by mixing 25 parts by weight of the active substance with 3 parts by weight of calciumlignin sulfonate, 2 parts by weight of dibutylnaphthalenesulfonate and 70 parts by weight of kaolin.

14. Liquid concentrates of the active substances according to the invention have been prepared by dissolving 10 parts by weight of the active substance in dimethylformamide to which a small amount of cyclohexanone may be added and by subsequently adding to the obtained solution from 6 to 7 parts by weight of an emulsifier, such as a mixture of nonylphenolpolyglycolether and alkaline-earth alkylbenzenesulfonate.

15. The active substances according to the invention have been dispersed in water in concentrations of 100. 30, 10, 3, 1, 0.3 and 0.1 mg of the active substance per liter of aqueous dispersion. Young Brussels sprout plants are sprayed with an aqueous dispersion of the substance according to the invention to be investigated, until the dispersion dr ps off. After the plants have dried they are placed in Perspex cylinders and then each infected with 5 larvae of *Pieris brassica* (catepillars of the White cabbage butterfly). The cylinders are then covered with gauze and stored at a temperature of 24° C. and a relative humidity of from 60–70%. After 5 days the mortality percentage is ascertained. Each test is conducted in triplicate. The results of the tests are given in the following Table. The meanings of the symbols used in the Table are:

+ = from 90–100% mortality
± = from 50–90% mortality
− = less than 50% mortality.

TABLE

Biocidal activity on larvae of *Pieris brassica*

| Compound | Activity concentration expressed in mg of active substance per liter | | | | | | |
|---|---|---|---|---|---|---|---|
| | 100 | 30 | 10 | 3 | 1 | 0,3 | 0,1 |
| N-(2,6-dichlorobenzoyl)-N'-(3,4-dichlorphenyl) urea | + | + | + | + | + | ± | − |
| N-(2,6-difluorobenzoyl)-N'-(3,4-dichlorophenyl) urea | + | + | + | + | + | + | − |
| N-(2,6-dimethylbenzoyl)-N'-(3,4-dichlorophenyl) urea | + | ± | ± | ± | ± | | |
| N-(2,6-dichlorobenzoyl)-N'-(4-chlorophenyl) urea | + | + | + | + | + | + | + |
| N-(2,6-dimethylbenzoyl)-N'-(4-chlorophenyl) urea | + | + | + | | | | |
| N-(2,6-dichlorobenzoyl)-N'-(2,4-dichlorophenyl) urea | + | + | + | − | | | |
| N-(2,6-dichlorobenzoyl)-N'-(4-cyclopropylphenyl) urea | + | + | + | + | ± | − | |
| N-(2,6-dichlorobenzoyl)-N'-(3-chloro-4-iodo-phenyl) urea | + | + | + | ± | − | | |
| N-(2,6-dichlorobenzoyl)-N'-(3-chloro-4-bromo-phenyl) urea | + | + | + | − | | | |
| N-(2,6-dichlorobenzoyl)-N'-(4-isopropylphenyl) urea | + | + | + | ± | − | | |
| N-(2,6-dichlorobenzoyl)-N'-(3,4-dibromophenyl) urea | + | + | + | − | | | |
| N-(2,6-dichlorobenzoyl)-N'-(4-fluorophenyl) urea | + | + | + | ± | − | | |
| N-(2,6-dichlorobenzoyl)-N'-(3-trifluoromethyl-phenyl) urea | + | + | + | − | | | |
| N-(2,6-dichlorobenzoyl)-N'-(4-n. butylphenyl) urea | + | + | + | + | + | − | |
| N-(2,6-dichlorobenzoyl)-N'-(3-chloro-4-methyl-sulfonylphenyl) urea | + | + | + | ± | − | | |
| N-(2,6-dichlorobenzoyl)-N'-(4-t.butyphenyl) urea | + | + | + | + | + | ± | − |
| N-(2,6-dichlorobenzoyl)-N'-(3,4-difluorophenyl) urea | + | + | + | + | + | ± | − |
| N-(2,6-dichlorobenzoyl)-N'-(2,4-difluorophenyl) urea | + | + | + | + | ± | − | |
| N-(2,6-dichlorobenzoyl)-N'-(4-bromophenyl) urea | + | + | + | + | + | + | − |
| N-(2,6-dichlorobenzoyl)-N'-(2,5-difluro-4-bromo-phenyl) urea | + | + | + | + | − | | |
| N-(2,6-dichlorobenzoyl)-N'-(4-iodophenyl) urea | + | + | + | + | + | ± | − |
| N-(2,6-dichlorobenzoyl)-N'-(3-fluoro-4-chloro-phenyl) urea | + | + | + | + | + | + | − |
| N-(2,6-dichlorobenzoyl)-N'-(4-phenylphenyl) urea | + | + | + | − | | | |
| N-(2,6-dichlorobenzoyl)-N'-(4-cyanophenyl) urea | + | + | + | + | ± | − | |
| N-(2,6-dichlorobenzoyl)-N'-(3-fluoro-4-bromo-phenyl) urea | + | + | + | + | + | + | − |
| N-(2,6-dichlorobenzoyl)-N'-(3-fluoro-4-iodo-phenyl) urea | + | + | + | + | + | | |
| N-(2,6-dichlorobenzoyl)-N'-(2-fluoro-4-iodo-phenyl) urea | + | + | + | + | + | + | − |
| N-(2,6-dichlorobenzoyl)-N'-(4-n. propylphenyl) urea | + | + | + | − | | | |
| N-(2,6-dichlorobenzoyl)-N'-(4-trifluoromethyl-phenyl) urea | + | + | + | + | + | + | + |
| N-(2,6-dichlorobenzoyl)-N'-(3-cyclopropylphenyl) urea | + | + | + | − | | | |
| N-(2,6-dichlorobenzoyl)-N'-(2-methyl-4-chloro-phenyl) urea | + | + | + | − | | | |
| N-(2,6-dichlorobenzoyl)-N'-(4-sec.butylphenyl) urea | + | + | + | | | | |
| N-(2,6-dichlorobenzoyl)-N'-(4-isobutylphenyl) urea | + | + | + | | | | |
| N-(2,6-dichlorobenzoyl)-N'-(4-ethylphenyl) urea | + | + | + | | | | |
| N-(2,6-dichlorobenzoyl)-N'-(4-n.dodecylphenyl) urea | | | | | | | |
| N-(2,6-dichlorobenzoyl)-N'-(4-benzylphenyl) urea | + | + | + | | | | |

TABLE-continued

Biocidal activity on larvae of *Pieris brassica*

| Compound | \multicolumn{7}{c}{Activity — concentration expressed in mg of active substance per liter} |||||||
|---|---|---|---|---|---|---|---|
|  | 100 | 30 | 10 | 3 | 1 | 0.3 | 0.1 |
| N-(3,6-dibromebenzoyl)-N'-(3,4-dichlorophenyl) urea | + | + | ± | ± | − |  |  |
| N-(3,6-dichlorobenzoyl)-N'-(methyl)-N'-(3,4-dichlorophenyl) urea | + | + | + | + | ± | − |  |
| N-(2,6-dichlorobenzoyl)-N'-(ethyl)-N'0(3,4-dichlorophenyl) urea | + | + | + | + | ± | − |  |
| N-(2,6-dichlorobenzoyl)-N'-(methyl)-N'-(4-t.butylphenyl) urea | + | + | + | + | ± | − |  |
| N-(2,6-dichlorobenzoyl)-N'-(methyl)-N'(4-bromophenyl) urea | + | + | + | + | + | − |  |
| N-(2,6-dichlorobenzoyl)-N'-(ethyl)-N'-(4-bromophenyl) uera | + | + | + | + | + | + | ± |
| N-(2,6-dichlorobenzoyl)-N'-(ethyl)-N'-(4-isopropylphenyl) urea | + | + | + | − |  |  |  |
| N-(2,6-dichlorobenzoyl)-N'-(ethyl)-N'-(4-n.butylphenyl) urea | + | + | + | + | − |  |  |
| N-(2,6-dichlorobenzoyl)-N'-(methyl)-N'-(4-chlorophenyl) urea | + | + | + | + | ± | − |  |
| N-(2,6-dichlorobenzoyl)-N'-(ethyl)-N'-4-chlorophenyl) urea | + | + | + |  |  |  |  |
| N-(2,6-dichlorobenzoyl)-N'(ethyl)-N-'-(4-t.butylphenyl) urea | + | + | + |  |  |  |  |
| N-(2,6-dichlorobenzoyl)-N'-(methyl)-N'(4-nitrophenyl) urea | + | + | + |  |  |  |  |
| 3-(2,6-dichlorobenzoyl)-1-(4-chlorophenyl)-parabanic acid | + | + | + |  |  |  |  |
| N-(2,6-dichlorobenzoyl)-N'-(2,4,5-trichlorophenyl) urea | + | + | ± | − |  |  |  |
| N-(2,6-dichlorobenzoyl)-N'-(phenyl) urea | + | + | ± | − |  |  |  |
| N-(2,6-dichlorobenzoyl)-N'-(4-nitrophenyl) urea | + | + | ± | − |  |  |  |
| N-(2,6-difluorbenzoyl)-N'-(4-trifluoromethyl)phenyl) urea | + | + | + | + | + |  |  |
| N-(2,6-difluorobenzoyl)-N'-(4-n. butylphenyl) urea | + | + | + | + | + |  |  |
| N-(2,6-difluorobenzoyl)-N'-(4-t.butylphenyl) urea | + | + | + | + | + |  |  |
| N-(2,6-difluorobenzoyl)-N'-(4-isopropylphenyl) urea | + | + | + | + | + |  |  |
| N-(2,6-difluorobenzoyl)-N'-(3-fluoro-4-iodophenyl) urea | + | + | + | + | + |  |  |
| N-(2,6-difluorbenzoyl)-N'-(3-fluoro-4-chlorophenyl) urea | + | + | + | + | + |  |  |
| N-(2,6-difluorobenzoyl)-N'-(3-trifluoromethylphenyl) urea | + | + | + | + | + |  |  |
| N-(2,6-difluorobenzoyl)-N'-(4-isobutylphenyl)-N'-(methyl) urea | + | + | + | + | + |  |  |
| N-(2,6-difluorobenzoyl)-N'-(4-chlorophenyl) urea | + | + | + | + | + |  |  |
| N-(2,6-difluorobenzoyl)-N'-(4-bromophenyl) urea | + | + | + | + | + |  |  |
| N-(2,6-difluorobenzoyl)-N'-(4-fluorophenyl) urea | + | + | + | + | + |  |  |
| N-(2,6-difluorobenzoyl)-N'-(4-thiomethylphenyl) urea | + | + | + | ± | − |  |  |
| N-(2,6-difluorobenzoyl)-n-(methyl)-N'-(4-chlorophenyl) urea | + | + | + |  |  |  |  |
| N-(2,6-difluorobenzoyl)-N-(methoxymehtyl)-N'-(3,4-dichlorophenyl) urea | + | + | + |  |  |  |  |
| N-2,6-dichlorobenzoyl)-N'-(3-chlorophenyl) urea | + | ± | ± | − |  |  |  |
| N-(2,6-dichlorobenzoyl)-N'-(5,6,7,8-tetrahydro-2-naphthyl) urea | + | − |  |  |  |  |  |
| N-(2,6-dichlorobenzoyl)-N'-(3,4-dioxymethylenephenyl) urea | + | ± | − |  |  |  |  |
| N-(2,6-dichlorobenzoyl)-N'-(4-dichlorocyclopropylphenyl) urea | + | + | ± | − |  |  |  |
| N-(2,6-dichlorobenzoyl)-N'-(4-methylsulfonyl) urea | + | ± | − |  |  |  |  |
| N-(2,6-dichlorobenzoyl)-N'-(3-bromo-4-chlorophenyl) uera | + | − |  |  |  |  |  |
| N-(2,6-dichlorobenzoyl)-N'-4-(p-chlorophenoxyphenyl) urea | + | ± | − |  |  |  |  |
| N-(2,6-dichlrobenzoyl)-N'-(3,5-dicyanophenyl) urea | + | ± | − |  |  |  |  |
| N-(2,6-dichlorobenzoyl)-N'-(2,5-difluorophenyl) urea | + | − |  |  |  |  |  |
| N-(2,6-dichlorobenzoyl)-N'-(3,4-dimethylphenyl) urea | + | − |  |  |  |  |  |
| N-(2,6-dichlorobenzoyl)-N'-(4-dimethylaminosulfonylphenyl) urea | ± | ± | ± | − |  |  |  |
| N-(2,6-dichlorobenzoyl)-N'-(4-phenylthiophenyl) urea | + | + | − |  |  |  |  |
| N-(2,6-dichlorobenzoyl)-N'-(4-benzoylphenyl) urea | + | + | ± |  |  |  |  |
| N-(2,6-dichlorobenzoyl)-N'-(4-pentylthiophenyl) urea | + | + | − |  |  |  |  |
| N-(2,6-dichlorobenzoyl)-N'-(3-dichlorocyclopropylphenyl) urea | ± | − |  |  |  |  |  |
| N-(2,6-dichlorobenzoyl)-N'-(4-pentylsulfonylphenyl) urea | + | ± | − |  |  |  |  |
| N-(2,6-dichlorobenzoyl)-N'-(4-n. octylphenyl) urea | + | ± | − |  |  |  |  |
| N-(2,methoxybenzoyl)-N'-(3,4-dichlorophenyl) urea | + | ± | − |  |  |  |  |
| N-(2-chlorobenzoyl)-N'-(3,4-dichlorophenyl) urea | + | ± | ± | − |  |  |  |
| N-(2-bromobenzoyl)-N'-(3,4-dichlorophenyl) urea | + | + | − |  |  |  |  |
| N-(2,6-dichlorobenzoyl)-N'-(hydroxy)-N'-(2,4,5-thrichlorophenyl) urea | ± | − |  |  |  |  |  |

TABLE-continued

Biocidal activity on larvae of *Pieris brassica*

| Compound | 100 | 30 | 10 | 3 | 1 | 0,3 | 0,1 |
|---|---|---|---|---|---|---|---|
| N-(2,6-dichlorobenzoyl)-N'-(pentyl)-N'-(3,4-dichlorophenyl) urea | + | + | − | | | | |
| N-(2,6-dichlorobenzoyl)-N'-(acetyl)-N'-(3,4-dichlorophenyl) urea | + | + | − | | | | |
| N-(2,6-dichlorobenzoyl)-N'-(ethoxycarbonyl)-N'-(3,4-dichlorophenyl) urea | + | + | − | | | | |
| N-(2,6-dichlorobenzoyl)-N'-(pentyl)-N'-(4-bromophenyl) urea | + | + | ± | + | | | |
| N-(2,6-dichlorobenzoyl)-N'-(methyl)-N'-(4-isopropylphenyl) urea | + | ± | − | | | | |
| N-(2,6-dichlorobenzoyl)-N'-(pentyl)-N'-(4-chlorophenyl) urea | + | + | ± | − | | | |
| N-(2,6-dichlorobenzoyl)-N'-(ethyl)-N'-(4-n.propylphenyl) urea | + | + | ± | − | | | |
| N-(2,6-dichlorobenzoyl)-N'-(ethyl)-N'-(4.sec.butylphenyl) urea | + | ± | ± | | | | |
| N-(2,6-dichlorobenzoyl)-N'-(ethyl)-N'-(4-isobutylphenyl) urea | + | + | − | | | | |
| N-(2,6-dichlorobenzoyl)-N'-(pentyl)-N'-(4-t.butylphenyl) urea | + | ± | − | | | | |
| N-(2,6-dichlorobenzoyl)-N'-(benzyl)-N'-(4-chlorophenyl) urea | + | + | ± | | | | |
| N-(2,6-dichlorobenzoyl)-N-(methoxymethyl)-N'-(4-chlorophenyl) urea | + | | | | | | |
| N-(2,6-dichlorobenzoyl)-N'-(methyl)-N'-(4-n.butylphenyl) urea | ± | + | ± | | | | |
| N-(2,6-dichlorobenzoyl)-N-(methyl)-N'-(3,4-dichlorophenyl) urea | + | + | ± | | | | |
| N-(2,6-dichlorobenzoyl)-N'-(methyl)-N'-(4-sec.butylphenyl) urea | + | ± | ± | | | | |
| N-(2,6-dichlorobenzoyl)-N'-(methyl)-N'-(4-isobutylphenyl) urea | + | ± | − | | | | |
| N-(2,6-dichlorobenzoyl)-N'-(methyl)-(4-n.propylphenyl)urea | + | − | | | | | |
| (3-(2,6-dichlorobenzoyl)-1-(p-chlorophenyl) hydantoin | + | − | | | | | |
| N-(2,6-dichlorobenzoyl)-N'-(4-chloropyridyl-2) urea | + | + | ± | − | | | |

EXAMPLE 16

The substances according to the invention are dispersed in water in concentrations of 1, 0.3, 0.1, 0.03 and 0.01 mg of active substance per liter of dispersion.

The aqueous dispersions are then inoculated with 20 one day old larvae of the yellow fever mosquito (*Aedes aegypti*) and maintained at a temperature of 25° C. The larvae are fed with malt yeast. After 6 days the mortality percentage is determined, taking account of the natural mortality. The results of this test are given in the following Table. The meanings of the symbols are:
+ = from 90–100% mortality
± = from 50–90% mortality
− = less than 50% mortality.

It should be noted that when the mortality percentage is not determined after 6 days but after 14 days it is much higher. The mortality percentage after 14 days may be derived reasonably satisfactorily from the following Table, which rotates to a waiting period of 6 days, by changing the "±" results to "+" results.

TABLE

Biocidal activity on larvae of Aedes aegypti

| Compound | 1 | 0,3 | 0,1 | 0,03 | 0,01 |
|---|---|---|---|---|---|
| N-(2,6-dichlorobenzoyl)-N'-(3,4-dichlorophenyl) urea | ± | ± | ± | ± | ± |
| N-(2,6-dichlorobenzoyl)-N'-(4-chlorophenyl) urea | ± | ± | ± | ± | − |
| N-(2,6-dichlorobenzoyl)-N'-(2,4-dichlorophenyl) urea | ± | ± | ± | − | |
| N-(2,6-dichlorobenzoyl)-N'-(4-cyclopropylphenyl) urea | + | ± | ± | − | |
| N-(2,6-dichlorobenzoyl)-N'-(3-chloro-4-bromophenyl) urea | + | ± | − | | |
| N-(2,6-dichlorobenzoyl)-N'-(4-fluorphenyl) urea | + | + | ± | − | |
| N-(2,6-dichlorobenzoyl)-N'-(3-trifluormethylphenyl) urea | + | + | + | ± | ± |
| N-(2,6-dichlorobenzoyl)-N'-(4-n.butylphenyl) urea | ± | ± | − | | |
| N-(2,6-dichlorobenzoyl)-N'-(2,5-difluoro-4-bromophenyl) urea | + | + | + | + | + |
| N-(2,6-dichlorobenzoyl)-N'-(3-fluoro-4-chlorophenyl) urea | + | + | + | + | + |
| N-(2,6-dichlorobenzoyl)-N'-(4-phenylphenyl) urea | + | + | + | + | + |
| N-(2,6-dichlorobenzoyl)-N'-(4-cyanophenyl) urea | + | + | + | − | |
| N-(2,6-dichlorobenzoyl)-N'-(4-trifluoromethylphenyl) urea | + | + | ± | ± | ± |
| N-(2,6-dichlorobenzoyl)-N'-(3-fluoro-4-iodophenyl) urea | + | + | + | + | + |
| N-(2,6-dichlorobenzoyl)-N'-(2-fluoro-4-iodophenyl) urea | + | + | + | + | + |
| N-(2,6-dichlorobenzoyl)-N'-(4.n.propylphenyl) urea | + | + | + | + | + |
| N-(2,6-dichlorobenzoyl)-N'-(3-cyclopropylphenyl) urea | + | + | − | | |
| N-(2,6-dichlorobenzoyl)-N'-(2-methyl-4-chlorophenyl) urea | + | + | − | | |
| N-(2,6-dichlorobenzoyl)-N'-(4-sec.butylphenyl) urea | + | + | + | | |
| N-(2,6-dichlorobenzoyl)-N'-(4-iso.butylphenyl) urea | + | + | ± | | |
| N-(2,6-dichlorobenzoyl)-N'-(4-ethylphenyl) urea | + | + | ± | | |
| N-(2,6-dichlorobenzoyl)-N'-(4-n.dodecylphenyl) urea | + | + | + | | |
| N-(2,6-dichlorobenzoyl) | | | | | |

TABLE-continued

Biocidal activity on larvae of Aedes aegypti

| Compound | Activity — Concentration expressed in mg of active substance per liter | | | | |
|---|---|---|---|---|---|
| | 1 | 0.3 | 0.1 | 0.03 | 0.01 |
| -N'-(4-benzylphenyl)urea | ± | ± | ± | | |
| N-(2,6-dibromobenzoyl)-N'-(3,4-dichlorophenyl)urea | ± | ± | ± | ± | |
| N-(2,6-dichlorobenzoyl)-N'-(methyl)-N'-(3,4-dichlorophenyl) urea | ± | ± | ± | − | |
| N-(2,6-dichlorobenzoyl)-N'-(ethyl)-N'-(3,4-dichlorophenyl) urea | ± | ± | ± | − | |
| N-(2,6-dichlorobenzoyl)-N'-(methyl)-N'-(4-bromophenyl) urea | + | + | + | − | |
| N-(2,6-dichlorbenzoyl)-N'-(ethyl)-N'-(4-bromophenyl) urea | + | + | + | − | |
| N-(2,6-dichlorobenzoyl)-N'-(ethyl-N'-(4-n.butylphenyl) urea | ± | ± | − | | |
| N-(2,6-dichlorobenzoyl)-N'-(methyl)-N'-(4-chlorophenyl) urea | + | + | − | | |
| N-(2,6-dichlorobenzoyl)-N'-(ethyl)-N'-(4-chlorophenyl) urea | + | + | − | | |
| 3-(2,6-dichlorobenzoyl)-1-(4-chlorophenyl)-parabanic acid | + | + | + | | |
| N-(2,6-dichlorobenzoyl)-N'-(4-methylphenyl) urea | ± | ± | ± | − | |
| N-(2,6-dichlorobenzoyl)-N'-(4-acetylphenyl) urea | ± | − | | | |
| N-(2,6-dichlorobenzoyl)-N'-(3-chloro-4-thiomethylphenyl) urea | ± | − | | | |
| N-(2,6-dichlorobenzoyl)-N'-(4-thiomethylphenyl) urea | + | ± | − | | |
| N-(2,6-dichlorobenzoyl)-N'-(3-chloro-4-nitrophenyl)urea | ± | − | | | |
| N-(2,6-dichlorobenzoyl)-N'-(3,4-dimethylphenyl) urea | ± | − | | | |
| N-(2,6-dichlorobenzoyl)-N'-(2-fluorophenyl) urea | + | + | − | | |
| N-(2,6-dichlorobenzoyl)-N'-(3-fluorphenyl) urea | ± | ± | − | | |
| N-(2,6-dichlorobenzoyl)-N'-(4-pentylithiophenyl) urea | + | + | + | − | |
| N-(2,6-dichlorobenzoyl)-N'-(4-methylthiomethylphenyl) | ± | ± | − | | |
| N-(2-chlorobenzoyl)-N'-(3,4-dichlorophenyl) urea | ± | ± | ± | | |
| N-(2-bromobenzoyl)-N'-(3,4-dichlorophenyl) urea | ± | ± | ± | − | |
| N-(2,6-dichlorobenzoyl)-N-(methyl)-N'-(3,4-dichlorophenyl) urea | ± | ± | ± | ± | ± |
| N-(2,6-dichlorobenzoyl)-N'-(pentyl)-N'-(4-bromophenyl) urea | + | + | − | | |
| N-(2,6-dichlorobenzoyl)-N'-(benzyl)-N'-(4-chlorophenyl) urea | + | + | − | | |
| N-(2,6-dichlorobenzoyl)-N-(methyl)-N'-(4-chlorophenyl) urea | + | + | + | | |
| N-(2,6-dichlorobenzoyl)-N-(methoxymethyl)-N'-4-chlorophenyl) urea | + | + | + | | |
| N-(2,6-dichlorobenzoyl)-N-(methoxymethyl)-N'-(3,4-dichlorophenyl) urea | + | + | + | | |
| N-(2,6-dichlorobenzoyl)-N-(methyl)-N'-(methyl)-N'-(3,4-dichlorophenyl) urea | + | + | − | | |
| N-(2,6-dichlorothiobenzoyl)-N'-(3,4-dichlorophenyl) urea | ± | ± | ± | − | |
| N-(2,6-dichlorobenzoyl)-N'-(3,4-dichlorophenyl) thiourea | ± | ± | | | |
| N-(2,6-dichlorothiobenzoyl)-N'-(3,4-dichlorophenyl) thiourea | + | + | + | ± | |

What is claimed is:

1. An insecticidal composition comprising an inert carrier and an insecticidally effective amount, as active ingredient, of a compound of the formula

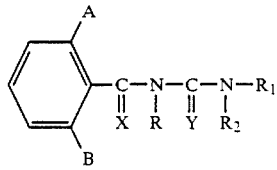

wherein
A is a hydrogen atom, a halogen atom, a methyl group, or a methoxy group;
B also is a hydrogen atom, a halogen atom, a methyl group, or a methoxy group, with the proviso that A and B are not both a hydrogen atom;
R is a hydrogen atom, an alkyl group, a hydroxy group, an alkoxy group, an alkoxymethyl group, an acyl group, or an alkoxycarbonyl group;
X and Y each are an oxygen atom or a sulfur atom;
$R_1$ is a hydrogen atom, an alkyl group that may be substituted with halogen, with alkoxy, with alkylthio, or with cyano, a 1-cycloalkenyl group, a benzyl group that may be substituted with halogen, a hydroxy group, an alkoxy group, an acyl group, an alkoxycarbonyl group, an alkoxythiocarbonyl group, an alkylsulfonyl group, or a phenylsulfonyl group; and
$R_2$ is substituted or non-substituted phenyl group or a pyridyl group that may be substituted with halogen, with nitro, with cyano, or with halogenated alkyl;
with the proviso that the active ingredient comprises a compound that is not included in any of the following paragraphs:
 (1) N-(2,6-dichlorobenzoyl)-N'-(4-cyanophenyl) urea;
 (2) N-(2-monochlorobenzoyl)-N'-(3,4-dichlorophenyl) urea.

2. The composition of claim 1, wherein the active ingredient comprises a compound that is not a N-(2-monohalobenzoyl)-N'-3,4-dichlorophenyl) urea.

3. A method of combatting insects in agriculture and horticulture comprising treating insect-infested areas with the insecticidal composition of claim 1.

* * * * *

UNITED STATES PATENT AND TRADEMARK OFFICE
CERTIFICATE OF CORRECTION

PATENT NO. : 4,920,135
DATED : April 24, 1990
INVENTOR(S) : Kobus Wellinga et al It is certified that error appears in the above-identified patent and that said Letters Patent is hereby corrected as shown below:

ON THE TITLE PAGE

Item [75] Inventors: "Rudolf Wulder" should read --Rudolf Mulder--.

Item [*] Notice: "subsequent to Feb. 24, 1993" should read
--subsequent to November 2, 1993--.

Column 28, (Claim 2) line 67, "3.4" should be preceded by --(--.

Signed and Sealed this

Eighteenth Day of February, 1992

*Attest:*

HARRY F. MANBECK, JR.

*Attesting Officer*     *Commissioner of Patents and Trademarks*